United States Patent [19]

King

[11] Patent Number: 4,638,251

[45] Date of Patent: Jan. 20, 1987

[54] METHOD AND APPARATUS FOR MEASURING FLOW OF NON-HOMOGENEOUS MATERIAL IN INCOMPLETELY FILLED FLOW CHANNELS

[75] Inventor: James D. King, San Antonio, Tex.

[73] Assignee: Southwest Research Institute, San Antonio, Tex.

[21] Appl. No.: 665,669

[22] Filed: Oct. 29, 1984

[51] Int. Cl.$^4$ .............. G01R 33/20; G01F 1/56; G01N 24/08

[52] U.S. Cl. ............................ 324/306; 324/300

[58] Field of Search ............ 324/306, 300, 316, 319, 324/303, 307; 73/861.08, 227

[56] References Cited

U.S. PATENT DOCUMENTS

| | | | |
|---|---|---|---|
| 3,820,392 | 6/1974 | Beck et al. | 73/861.08 |
| 4,202,211 | 5/1980 | Perry | 73/227 |

FOREIGN PATENT DOCUMENTS 0819657  4/1981  U.S.S.R. .............. 324/300

OTHER PUBLICATIONS

Genthe et al., NMR applied to Flow Measurement, Nov. 1968.
Abouelwafa et al., Optimization of Continuous Wave Nuclear Magnetic Resonance to Determine in Situ Volume Fractions and Individual Flow Rates in Two Component Mixtures, Rev. Sci. Instrum., 50(12), Dec. 1979.

Primary Examiner—Stewart J. Levy
Assistant Examiner—Scott M. Oldham

[57] ABSTRACT

In the preferred and illustrated embodiment, a method and apparatus for measuring the flow of non-homogeneous materials in an incompletely filled channel is set forth. In one embodiment, a NMR (or ESR) flow meter arrangement including a magnet forming the requisite magnetic field $H_o$ across a flow channel is incorporated. The magnet cooperates with a coil providing an NMR or ESR output signal from selected specie(s) or subatomic patricles (i.e. nuclei or unpaired electrons) in the material in the flow stream. It is desirable for the signal to be representative of the total amount of material in the flow stream. This signal may be in error, unable to sort out prospective combined variations due to (1) incomplete filling of the sensing volume or (2) a non-homogeneous composition of material. A composition sensor coil inscribing a very small volume in selected portions of the flow channel is included to form an NMR output signal indicative of composition, the small volume being filled for that sensor. Its output signal thus determines one of the two variables, and is input to a data combining circuit to indicate the flow volume from the two signals.

19 Claims, 4 Drawing Figures

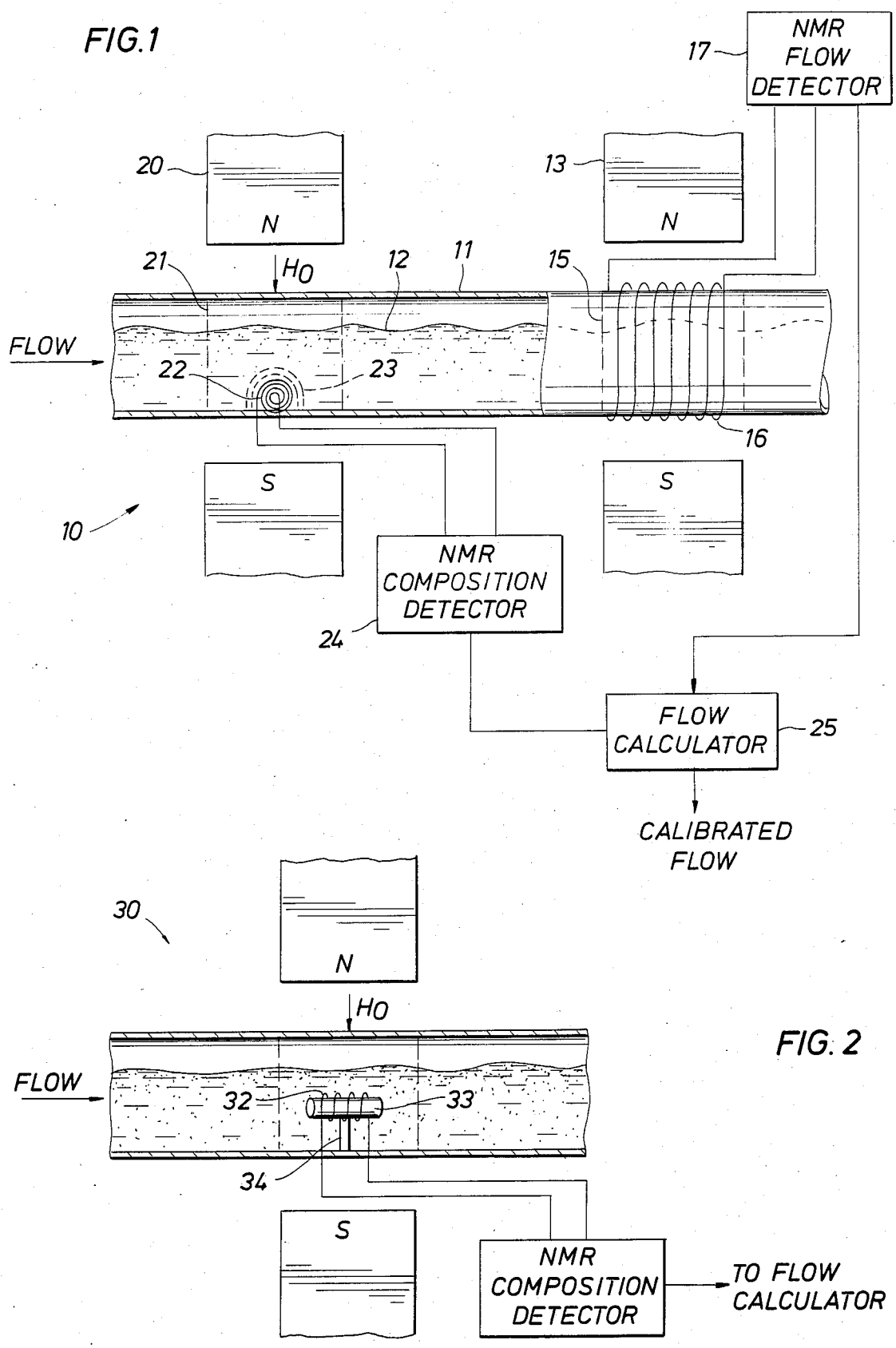

METHOD AND APPARATUS FOR MEASURING FLOW OF NON-HOMOGENEOUS MATERIAL IN INCOMPLETELY FILLED FLOW CHANNELS

BACKGROUND OF THE DISCLOSURE

An NMR flow meter can measure the flow of materials using NMR procedures provided most of the variables are fixed. A flow meter of such construction typically has a fixed sensitive region. That refers to the region which is exposed to the requisite magnetic field, that field being indicated by the symbol $H_o$. The device is not able to distinguish between changes in fill factor within the sensitive region or, non-homogeneous variations in composition of the flowing material.

This apparatus works quite well so long as one of the two important factors (non-homogeneous material composition and fill factor) is held constant, or only one is permitted to vary. As will be understood the response of the NMR detector system is based on population of a particular nuclei species within the sensing region. That population can be reduced either by incomplete filling or a non-homogeneous variation in the material. Generally, measuring devices can be used with pipes or conduits which are sized to enable complete filling. Sometimes, the application of the measuring device will not permit such a narrow constriction in the flow path of the material undergoing measurement.

This disclosure sets forth an auxiliary magnetic resonance detector. It can either be a nuclear magnetic resonance detector or an electron spin resonance detector (known as NMR and ESR). The auxiliary detector utilizes a small coil which defines a relatively small sensing region for the auxiliary detector. This small coil is usually positioned in the bottom portions of the conduit to assure that it is filled at all times. Thus, it is provided with 100% filling within its particular sensing region, and filling of this volume assures that the fill factor is meaningless to the signal provided by the auxiliary magnetic resonance detector. Thus, it is sensitive only to variations in homogeneity of the flowing material. The auxiliary detector therefore forms an output signal which may be described as a calibration factor. It is a calibration factor relating to the homogeneous material or absence of homogeneity in the flowing material.

The flow volume can then be determined from this data. Briefly, the flow volume is dependent on the two measurements from the two detector systems and constants which takes into account system parameters, proportionality, linear operation and the like. The actual flow volume can therefore be defined as being the function of the two output signals or is given by the relationship f(x,y) where the two variables are the output signals. This accomodates changes in composition and fill factor within the conduit.

One reference of note is Handel, U.S. Pat. No. 2,948,845. This disclosure is directed to a system which does not involve flowing materials. In Aske, U.S. Pat. No. 3,379,979 a system involving duel channel operation (see FIG. 3 thereof) is set forth. It does not concern measuring volume flowing in a pipe or conduit. In Auld, U.S. Pat. No. 4,286,216 a metal flaw detector is set forth. It works with disturbances in the field. Again, it is not particularly concerned with a flow system. In Abe, U.S. Pat. No. 3,932,805 magnetic field superimposition is described to obtain a controllable gradient in the field and hence a resonance frequency in the output data. This reference does not cooperate with a variable fill factor flow system.

In summary, this disclosure sets forth both a method and apparatus for making flow measurements in a situation involving partial filling of the flow path with materials which vary in composition as to the sensitive material detected by the flow measuring apparatus.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not be considered limiting of its scope, for the invention may admit to other equally effective embodiments.

FIG. 1 shows the flow measuring system of the present disclosure in schematic form wherein a pipe or other conduit is subject to irregular flow volume and variations in flow composition which are sensed by the detector apparatus of this disclosure;

FIG. 2 shows a composition detection coil for determining the concentration of selected nuclear species within the flowing material within a defined spatial region;

DETAILED DESCRIPTION OF THE PREFERRED EMBODIMENT

Figure 3:
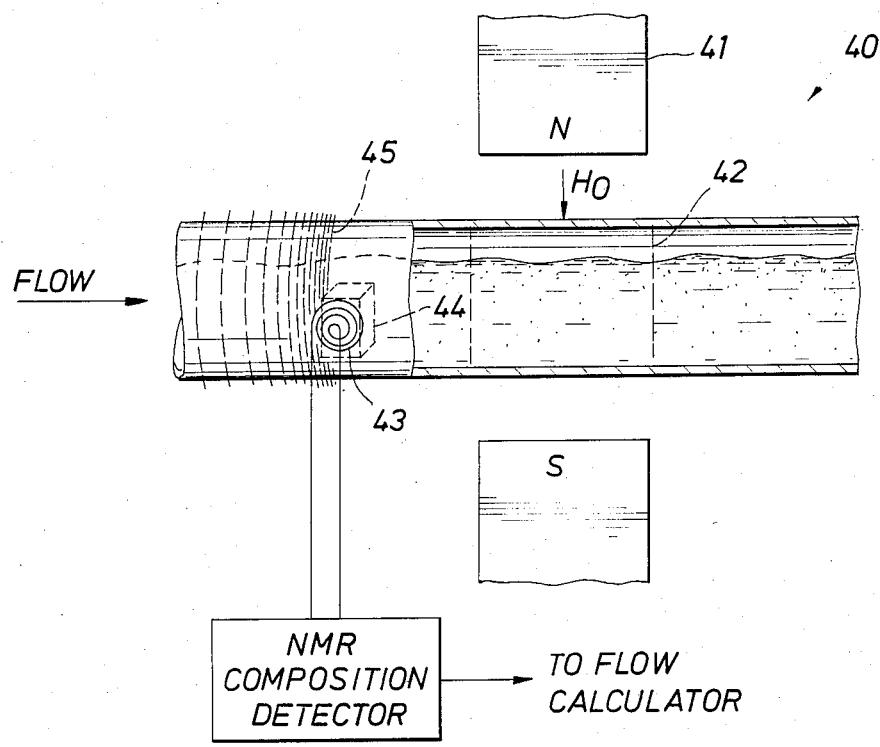
FIG. 3 shows an alternate arrangement wherein the concentration of selected nuclear species in the flowing material is determined within a region of reduced field intensity located in the field gradient.

In FIG. 1 of the drawings, the numeral 10 identifies a flow measuring system in accordance with the teachings of this disclosure. The system cooperates with a pipe 11. Preferably, the pipe is formed of a material which is not ferromagnetic and is able therefore to permit lines of flux to pass through the pipe for operation of the device. A material flows through the pipe and is identified by the numeral 12. The pipe or conduit can be a conveyor belt or other flow system. It can be a V-shaped trough. It can include other types of structures which conduct the flowing material 12. The material 12 is characterized by flowing at different rates and at different fill factors on the pipe 11. The pipe has a specific cross-sectional area. This defines the maximum capacity of the pipe. The volume may be substantially less than the maximum volume, filling only a part of the pipe volume, and hence reducing the total volumetric flow substantially below the sensitive region. The term "sensitive region" refers to that region or portion of the pipe which is exposed to a specific magnetic flux density $H_o$ and within the coil test volume. That region is between the poles of a magnet indicated at 13. The magnet forms a field which is located between the dotted lines at 15. This field is specified at $H_o$ to enable an NMR detector of the flowing material to operate at the corresponding frequency, $\omega_o$. The NMR detector incorporates a coil 16 around the pipe or conduit 11 and is connected with an NMR flowing material detector 17.

The flow detector 17 forms a measure of the flow through the sensitive region 15. Ordinarily, this will be an accurate measure of flow provided the flow velocity is known from either the NMR sensor or from some other source and provided one of the two following variables is fixed. The two variables are (1) the filling of the sensitive region and (2) the composition of the flowing material, namely, whether or not it is non-homogeneous in nature.

Under the assumption that one of these two variables is fixed, calibration factors for the NMR flow detector 17 will make it operate to provide an accurate measure of flow. This is also true in the use of an ESR flow measuring system. The problem confronted by this apparatus is not that simple. It is assumed that both variables will fluctuate. This can occur in many situations too numerous to exemplify. In that event, another magnet 20 is installed adjacent to the pipe or conduit 11. It forms a magnetic field with a field intensity of $H_o$. This field is located at the region 21. As will be observed, the magnet 20 can be omitted and the magnet which defines the sensitive region 15 can be widened. This will form a longer magnetic field assuming that the requisite field intensity $H_1$ is appropriate for the operating frequency of the two NMR detectors. For illustrative purposes, FIG. 1 shows two separate magnets and it will be assumed that the field intensity for the two can be the same or different. The two magnets are thus spaced apart in FIG. 1.

The magnet 20 forms a field of requisite intensity through the flowing material 12. A small detector coil 22 is positioned in the lower portions of the pipe 11. It either can be installed adjacent to the pipe or actually protrude into the pipe. The axis of the coil 22 can be parallel to and below the axis of the pipe 11; alternatively, the axis of the coil 22 can be transverse as illustrated in FIG. 1. Whatever the case, the coil 22 detects in a sensitive region which is within the dotted line at 23. This sensitive region is preferably at the bottom of the pipe or conduit. That is, it is sufficiently low that the sensitive region 23 is always filled with the flowing material 12. Moreover, it is sufficiently low and small that it is maintained full of the flowing material 12 at the minimum flow rates of the material. As an easy example, the sensitive volume may extend 20% into the conduit 11; if the conduit is a round pipe, this actually is a very small volumetric throughput to assure that the sensitive volume 23 is filled.

The coil 22 is connected with an NMR composition detector 24. It is operated to obtain a measure of the nuclei of interest to the system. The nuclei of interest might be hydrogen as one example. It might be nitrogen in another example. The particular nuclei can be designated. It is important to note that the volume 23 is filled with the material. In other words, the fill factor within the volume 23 is 100%.

The output signal of the NMR composition detector is therefore proportional to variations in the concentration of selected nuclei, or related nuclei within specified states in the material itself. That is, it is not sensitive to variations in volumetric flow. It is exposed to a full measure of material 12 within the volume, thereby assuring that the only variable observed within the volume 23 relates to the consistency of the detected nuclei in composition 12. In other words, the NMR composition detector 24 outputs a signal which is proportional to the population of the nuclei of interest which is a function of the homogeneous material 12 in the pipe 11.

The NMR composition detector 24 forms an output signal applied to a flow calculator 25. The flow calculator determines the volumetric flow. The flow velocity is preferrably determined by the NMR detector 17 but may be provided by other flow velocity sensors as are well know. The volumetric flow is a function of the two variables which are output by the NMR flow detector 17 and the NMR composition detector 24. The flow calculator thus determines the instantaneous product of flow velocity times flow concentration and forms an output signal which is indicative of volumetric flow incorporating a constant of proportionality. This constant can be obtained by suitable calibration techniques. The signal from the NMR composition detector 24 is a function of only one variable. This enables the two signals to be used in combination with the flow velocity to form the output of the flow volume through the system.

In FIG. 2 of the drawings, an alternate embodiment is illustrated at 30. This embodiment locates the composition detector coil 32 supported on a coil form 33. The coil form 33 is axially hollow. It is supported by an upstanding post 34. It is located to intercept flowing material in the pipe, and it is positioned to assure that it is always filled. The flow calculator is provided with a signal from the NMR composition detector incorporated in FIG. 2. The structure of FIG. 2 differs primarily in the positioning of the NMR composition detector coil 32 and the related sensitive region for that coil. In contrast with the structure of FIG. 1, the two coils differ primarily in position and orientation relative to the flowing material 12.

In FIG. 3 of the drawings, an arrangement for cooperation with a single magnet is illustrated. This embodiment is identified by the numeral 40. It incorporates a single magnet 41 which forms the requisite field intensity $H_o$ in the region at 42. This is a sufficient intensity to cause the NMR flow detector 17 to operate. A composition detector coil 43 is located adjacent to or within the pipe. It is located to operate in a field of reduced intensity, perhaps about 50% of $H_o$. Whatever the intensity is, there is a requisite sensitive region 44 associated with the sensor coil 43. This is relatively small and is again located in the bottom portions of the pipe. More importantly, the volume 44 is defined by a value of magnetic field intensity which is in the gradient portions to the exterior of the uniform field 42. The uniform field 42 thus forms the gradient magnetic field 45 which includes the sensitive region 44. This is the volume which is tested by the NMR composition detector. As arranged in FIG. 1, the composition detector forms an output signal to the flow calculator.

Figure 4:
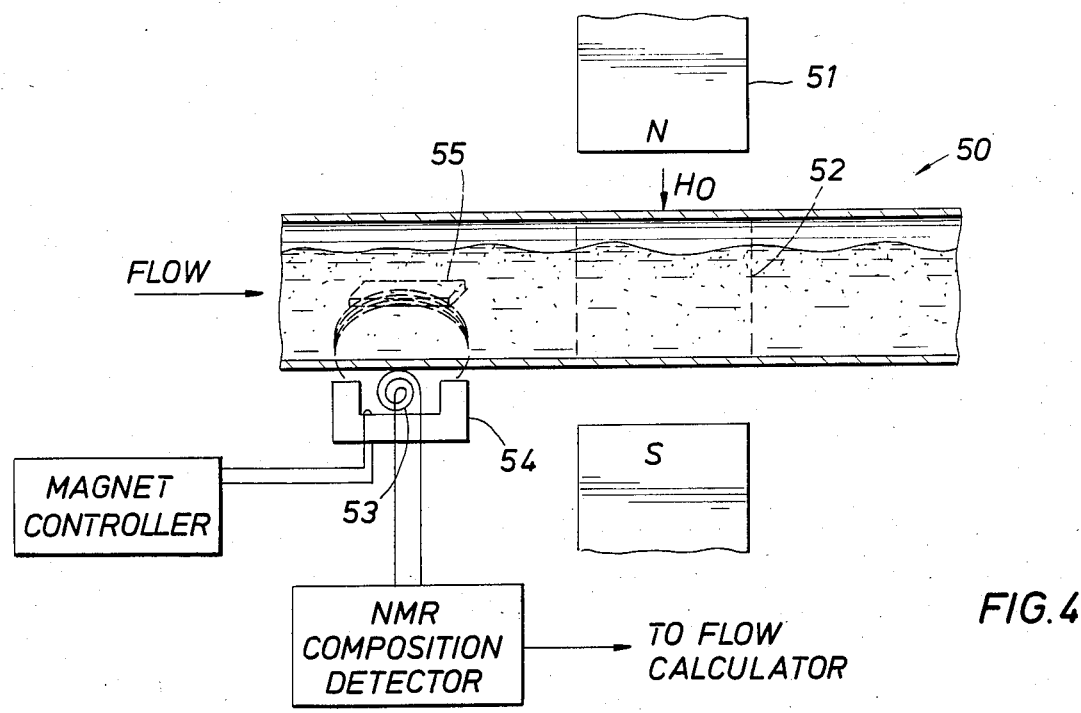
FIG. 4 shows an alternate embodiment wherein the concentration detector is located on the exterior of the flow conduit and is sensitive to concentration of nuclei within on the interior of the conduit.

The embodiment of FIG. 4 is identified by the numeral 50. Again, it incorporates a magnet 51 which forms a field intensity $H_o$ in the region identified at 52. The composition detector coil 53 is located on the exterior of the pipe. It is in the throat of a U-shaped magnet 54. The magnet 54 forms a field of specified intensity and gradient to thereby define a sensitive volume 55. The volume 55 has the necessary field intensity to cooperate with the coil 53 and associated NMR composition detector to thereby obtain NMR detection. The volume 55 is located sufficiently low in the pipe that it is always filled with the flowing material. Thus, it is outside the sensitive region 52 and defines its own sensitive region 55. Again, the coil 53 is connected to the NMR composition detector which in turn provides an output signal to the flow calculator. The magnet 54 may be oriented parallel to the axis of the pipe as illustrated in FIG. 4 or perpendicular to the pipe axis.

Many variations have been shown in the arrangement of the coil and magnet to assure that the composition detector operates without interference with the NMR flow detector. To this end, the two detectors may operate on the same magnetic field or require different field intensities. The arrangement at 40 enables the use of a single magnet and different field intensities. With a fixed physical arrangement between magnet and pipe, the field intensity for the volume 44 can be made a specific fraction of the field intensity $H_o$. In the arrangement at 50, the two field intensities can be completely unrelated to one another and may vary accordingly. In the arrangement shown in FIG. 1, the two fields are quite independent of one another.

The term NMR as used in the claims refers to various species of sub-atomic particles such as a nuclei or unpaired electron. Thus, this definition might be thought of as referring to an electron (testing with ESR), where the commonality of stimulus and response seems to reasonably include both types of particles (nuclei or electrons).

While the foregoing is directed to the preferred embodiment, the scope is determined by the claims which follow.

What is claimed is:

1. A flow measuring apparatus cooperative with a flow stream of non-homogeneous material wherein the volume thereof fluctuates to less than the full volume of the conduit for the flowing stream, the apparatus comprising:
   (a) a nuclear magnetic resonance flow detector including a magnet forming a field in a sensitive region of the flow stream and also including a first detection coil for detecting the population of a particular nuclear species within that sensitive region and forming an output signal indicative of the flow velocity thereof;
   (b) a second coil comprising a composition sensor positioned relative to the flowing material and defining a sensitive volume therein in conjunction with a cooperative magnetic field intensity, thereby defining a sensitive region for said second coil, said second coil being positioned relative to the flowing material to be fully filled during measurements with the flowing material, said second coil being connected with a nuclear magnetic resonance composition detector means forming an output signal indicative of the concentration of the selected nuclear species in the flowing material; and
   (c) flow calculator means provided with the output (1) from said composition detector means and (2) from said flow detector to form an output indicative of the quantity of flowing non-homogeneous materials without regard to the volume filling the sensitive region of said flow detector.

2. The apparatus of claim 1 wherein said second coil is constructed with a sensitive region relatively positioned in the conduit to observe the flowing material at low volumes therethrough, and also incorporates a means positioning said coil axially parallel to the path of flow of the material.

3. The apparatus of claim 1 wherein said second coil is constructed with a sensitive region relatively positioned in the conduit to observe the flowing material at low volumes therethrough, and also incorporates a means positioning said coil axially transverse to the path of flow of the material.

4. The apparatus of claim 1 wherein said second coil is constructed with a sensitive region relatively positioned in the conduit to observe the flowing material at low volumes therethrough, and also incorporates a means positioning said second coil in the magnetic field of said magnet to obtain the cooperative magnetic field intensity.

5. The apparatus of claim 1 wherein said second coil is constructed with a sensitive region relatively positioned in the conduit to observe the flowing material at low volumes therethrough, and also incorporates a means positioning said second coil in a separate magnetic field.

6. Measuring apparatus for determining the population of a particular nuclear species in a material of a non-homogeneous nature flowing through a pipe or channel for the flowing material wherein the volume in the pipe or channel fluctuates to less than the full volume thereof, the apparatus comprising:
   (a) magnetic resonance detector means including a magnet forming a field having a sensitive region acting fully across the pipe or conduit and also incorporating detection coil means for detecting the population of a particular resonant species within that region and forming an output signal indicative of the species within the pipe or conduit;
   (b) magnetic resonance detector means cooperative with a magnetic field intensity defining a sensitive region which is less than the full volume of the pipe or conduit having a specified intensity wherein that region is fully filled with the flowing material; and
   (c) means connected to said (a) means and (b) means for determining instantaneous quantity of the species of interest as a function of the signals from said (a) and (b) means.

7. The apparatus of claim 6 wherein a single magnet means forms a magnetic field for said (a) means and a magnetic field for said (b) means, said magnetic fields being formed by a single magnet.

8. The apparatus of claim 6 wherein two separate magnets means forms a magnetic field for said (a) means and a magnetic field for said (b) means, said magnetic fields being formed by two separate magnets.

9. A method of determining the volume flow a non-homogeneous material where the flow fills the flow path by less than the maximum permitted therethrough, the method comprising the steps of:
   (a) within a small sensitive region in the portions of the flow path where material is always flowing, measuring the flowing material to determine variations in composition as indicated by the particle magnetic resonance response of a selected particle species of interest and forming an output signal thereof;
   (b) measuring with a particle magnetic resonance sensitive means the materials flowing along the path in a sensitive region which encompasses the entire flow path cross section and wherein the fill factor in that region can vary from 100% downwardly, and forming an output signal indicative thereof; and
   (c) utilizing the signals provided in both of the above steps to determine the flow volume as a function of variations in the material as a result of non-homogeneous material and also variations in the fill factor within the sensitive region.

10. The method of claim 9 wherein the small sensitive region is defined by a coil cooperative with a magnetic field, and within said small sensitive region, the magnetic flux intensity is maintained at a level to obtain particle magnetic resonance response.

11. The method of claim 10 wherein said small sensitive region is formed by positioning a coil to the exterior of the flowpath and said coil is coupled into said small sensitive region on the interior of the flowpath.

12. The method of claim 11 wherein said small sensitive region is defined by positioning a magnet to the exterior of said flow path, and said magnet has lines of flux defining a specified magnetic field intensity within the flow path.

13. The method of claim 9 including a single magnet means positioned to form a uniform field having a specified intensity within a region to enable the step of measuring across the entire flow path, and further wherein said small sensitive region is defined by only a portion of that magnetic field.

14. The method of claim 9 including the step of measuring flow velocity along the flow path and multiplying the flow velocity periodically by the flow volume to obtain the flow rate along the flow path.

15. The method of claim 14 including the step of integrating as a function of time to obtain total flow volume over an interval of time.

16. The method of claim 9 wherein measuring flow volume through a pipe includes the step of forming the small sensitive region on the interior of the pipe with an coil means and a magnet means, wherein either the coil means or the magnet means is positioned on the exterior of the pipe and the two are positioned to interact within the small sensitive region on the interior of the pipe.

17. The method of claim 9 including the step of forming a magnetic field across the flow path and positioning a multi-turn coil around the flow path wherein the coil is operatively coupled with a magnetic field formed across the entire flow path.

18. The method of claim 9 including the step of measuring the resonance of a selected nuclei.

19. The method of claim 9 including the step of measuring the population of unpaired electrons.

* * * * *